United States Patent
Ikeda et al.

(10) Patent No.: US 9,278,063 B2
(45) Date of Patent: *Mar. 8, 2016

(54) PRESS-COATED ORALLY-DISINTEGRATING TABLETS

(75) Inventors: Yuki Ikeda, Ibaraki (JP); Yasushi Ochiai, Ibaraki (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/513,956

(22) PCT Filed: Dec. 10, 2010

(86) PCT No.: PCT/JP2010/072203
§ 371 (c)(1),
(2), (4) Date: Jun. 5, 2012

(87) PCT Pub. No.: WO2011/071139
PCT Pub. Date: Jun. 16, 2011

(65) Prior Publication Data
US 2012/0237602 A1    Sep. 20, 2012

(30) Foreign Application Priority Data
Dec. 11, 2009    (JP) ................ 2009-281216

(51) Int. Cl.
*A61K 9/36* (2006.01)
*A61K 9/00* (2006.01)
*A61K 9/28* (2006.01)

(52) U.S. Cl.
CPC ............... *A61K 9/0056* (2013.01); *A61K 9/284* (2013.01); *A61K 9/2886* (2013.01)

(58) Field of Classification Search
None
See application file for complete search history.

(56) References Cited

U.S. PATENT DOCUMENTS

| 5,047,246 | A | * | 9/1991 | Gallian et al. | 424/464 |
|---|---|---|---|---|---|
| 5,958,453 | A | | 9/1999 | Ohno et al. | |
| 6,287,596 | B1 | * | 9/2001 | Murakami et al. | 424/464 |
| 6,740,339 | B1 | | 5/2004 | Ohkouchi et al. | |
| 2004/0113319 | A1 | * | 6/2004 | Kondo et al. | 264/319 |
| 2004/0180085 | A1 | * | 9/2004 | Ohkouchi et al. | 424/465 |
| 2005/0202082 | A1 | | 9/2005 | Hibino et al. | |
| 2008/0317851 | A1 | * | 12/2008 | Appel et al. | 424/465 |

FOREIGN PATENT DOCUMENTS

| EP | 1 302 304 | 4/2003 |
|---|---|---|
| JP | 10-182436 | 7/1998 |
| JP | 2001-58944 | 3/2001 |
| WO | 01/98067 | 12/2001 |
| WO | 03/028706 | 4/2003 |
| WO | 2004/000197 | 12/2003 |
| WO | 2005/097041 | 10/2005 |

OTHER PUBLICATIONS

Hancock et al. "The relative densities of pharmaceutical powders, blends, dry granulations and immediate-release tablets," Pharmaceutical Technology, 27:64-80, 2003.*
International Preliminary Report on Patentability issued Dec. 12, 2011 in International (PCT) Application No. PCT/JP2010/072203, of which the present application is the national stage.
International Search Report issued Feb. 22, 2011 in International (PCT) Application No. PCT/JP2010/072203, of which the present application is the national stage.
Chinese Office Action issued Apr. 15, 2013 in Chinese counterpart Application No. 201080063719.X, with English translation.
Chinese Search Report issued Apr. 15, 2013 in Chinese counterpart Application No. 201080063719.X, with English translation.
Guidance for Industry Orally Disintegrating Tablets, U.S. Department of Health and Human Services Food and Drug Administration, Center for Drug Evaluation and Research, Dec. 2008, pp. 1-3.
Handbook of Pharmaceutical Excipients, $5^{th}$ edition, Pharmaceutical Press, pp. 611-616 (2005).
Handbook of Pharmaceutical Excipients, $5^{th}$ edition, Pharmaceutical Press, pp. 214-216 (2005).
English Version of the Japanese Pharmacopoeia, $15^{th}$ edition, pp. 408-411 and 546-547 (2006).
Shimizu et al. "Formulation Design of orally-disintegrating tablet prepared by OSDrC-OD technique, Abstracts from PCLM the $3^{rd}$ symposium", Rapid Orally-Disintegrating Tablet on Present Situation and Visions for Future, Jan. 2009, pp. 93-96 (with partial English translation).
Ozeki, Yuichi, "One-Step Dry Coated Tablets (OSDRC®): Process Development and Study of their physical Characteristics", J. Jpn. Soc. Pharm. Mach. & Eng., vol. 14, No. 4, 2005 (with partial English translation).
Supplementary European Search Report issued Oct. 8, 2013 in corresponding European Application No. 10 83 6058.

* cited by examiner

*Primary Examiner* — David J Blanchard
*Assistant Examiner* — Alissa Prosser
(74) *Attorney, Agent, or Firm* — Wenderoth, Lind & Ponack, L.L.P.

(57) ABSTRACT

The purpose of the invention is to provide a press-coated orally-disintegrating tablet having a powder/granular material with poor formability in its inner core, which has an excellent disintegrability and a suitable hardness as a whole tablet. Furthermore, the invention is a press-coated orally-disintegrating tablet with an outer layer surrounding an inner core wherein the inner core has a thickness in the range of 30 to 80% per that of the whole tablet, and the outer layer comprises (a) microcrystalline cellulose, (b) a sugar or a sugar alcohol, and (c) one or more particular ingredients selected from the group consisting of crospovidone, starches, low-substituted hydroxypropylcellulose and carmellose.

14 Claims, No Drawings

PRESS-COATED ORALLY-DISINTEGRATING TABLETS

TECHNICAL FIELD

The present invention relates to press-coated orally-disintegrating tablets. In particular, the invention relates to a press-coated formulation comprising an inner core containing a powder/granular material with poor formability and an outer layer surrounding the inner core, which exhibits a suitable hardness and an excellent disintegrability in the oral cavity as a final formulation (hereinafter, also referred to as "press-coated orally-disintegrating tablet"). In detail, the invention relates to a press-coated orally-disintegrating tablet wherein the outer layer rapidly disintegrates even when the tablet is taken with a small amount of water or without water, and then the granules or powders in the inner core are dispersed in the oral cavity.

BACKGROUND ART

Due to an aging society, there have been many attempts to develop orally-disintegrating tablets which can be easily taken by elderly people who have difficulty or trouble in swallowing tablets. Accordingly, there are growing demands for developing orally-disintegrating tablets containing various active ingredients. In case that an active ingredient has a bitter taste, the masking of the bitter taste may be necessary to formulate it into orally-disintegrating tablets and the like. Also, controlled release of an active ingredient may be necessary for increasing the bioavailability of the active ingredient. However, many of such functional particles tend to give some adverse affects on the formability of tablets (for example, they lack sufficient hardness when homogeneously distributed in a tablet), and thus it is necessary to add a large amount of additives such as an excipient and a binder to avoid the adverse affects, which inevitably leads the tablets to be in an inconvenient big size.

Patent Reference 1 discloses a press-coated rapidly disintegrating tablet as a unique form which has not been well known before. Press-coated tablets have a double-layered structure consisting of an inner core and an outer layer, and they have been attracting attentions as a novel technique for formulating tablets. However, the press-coated formulations disclosed in Patent Reference 1 are designed focusing on the solubility and degradability of the inner core, and the ingredients of both the inner core and the outer layer comprise ingredients with formability (for example, it appears that the ingredients of the inner core in Patent Reference 1 has formability and a certain hardness, as figured out in the results of Example 2 in which only the ingredients of the inner core were compressed into tablets). Thus, Patent Reference 1 does not try to apply powder/granular material with poor formability to the ingredients of the inner core, and the document discloses only a limited range of ingredients applicable to the inner core. Additionally, Patent Reference 1 discloses a combination of "microcrystalline cellulose" and "a sugar or a sugar alcohol" as an ingredient of the outer layer of the press-coated tablet, but it fails to disclose a combination which further comprises the "particular ingredients" of the present invention.

Furthermore, the particular ingredients of the present invention which are essential for the outer layer (e.g. carmellose, low-substituted hydroxypropylcellulose, natural starches, and/or crospovidone) are disclosed as a dissolution/disintegration accelerator of the inner core in Patent Reference 1 (see, page 9, lines 17 to 26). In detail, Patent Reference 1 explains that the outer layer comprises ingredients with good formability, and preferably it further comprises ingredients with good solubility and/or disintegrability; while the inner core also comprises ingredients with good solubility and/or disintegrability, and it may further comprise a dissolution/disintegration accelerator (see, page 8, lines 14 to 17). Moreover, Patent Reference 1 indicates that said inner core and outer layer are used to prepare a molded product having a double-layered structure wherein only the outer layer, which needs hardness, has a good formability whereas the inner core has an excellent solubility/disintegrability; and its inventors thus completed a molded product having a rapid dissolving/disintegration time with sufficient formability (see, page 5, lines 5 to 11 and abstract). Namely, it seems that the molded product in Patent Reference 1 exhibits its characteristics by containing ingredients such as dissolution/disintegration accelerators only in the inner core (i.e. excluding them from the outer layer). Conversely, the particular ingredients in the present invention are essential ingredients for the outer layer and therefore the particular ingredients in the present invention are used in an opposite manner to the ingredients in the invention of Patent Reference 1.

Patent Reference 2 discloses some trials of applying microcapsule-like granules to the ingredients of the inner core regarding the formulation in Patent Reference 1 described above. In detail, Patent Reference 2 discloses some studies on applying microcapsule-like granules to the inner core of the press-coated tablet, and some successful examples of press-coated formulations containing microcapsule-like granules in their inner cores which were prepared using the outer layers comprising lactose and microcrystalline cellulose according to a given method. Patent Reference 2 discloses an invention of press-coated tablets containing microcapsule-like granules in their inner core, but fails to disclose or suggest studies on applying the press-coated tablets to orally-disintegrating tablets. Additionally, in Patent Reference 2, there is no study about applicable ingredients for the outer layer in the press-coated formulation containing microcapsule-like granules in its inner core, other than lactose and microcrystalline cellulose. Of course, Patent Reference 2 does not disclose the combination of the essential ingredients for the outer layers of the present invention. Moreover, Patent Reference 2 fails to disclose mannitol as an ingredient of the outer layer of the press-coated formulation.

Patent Reference 3 refers to an orally disintegrating tablet comprising mannitol, but does not clearly disclose press-coated formulations.

[Patent Reference 1] WO 2003/028706 A1
[Patent Reference 2] WO 2005/097041 A1
[Patent Reference 3] JP 2001-058944 A

SUMMARY OF INVENTION

Technical Problem

Orally disintegrating tablets mean tablets which rapidly disintegrate in the oral cavity. In general, the hardness and disintegrability of tablets are conflicting factors. In case that the hardness is increased, then the disintegrability will be decreased; whereas in case that the disintegrability is increased, then the hardness will be decreased. Thus, it is difficult to attain both a desirable hardness and disintegrability in determining the formulation of orally disintegrating tablets.

In order to develop an orally disintegrating tablet comprising various functional ingredients/particles, it is necessary to devise some formulation design. It is because, if the ingredients/particles are homogeneously dispersed in the tablet, particularly if they have adverse effects on the formability, it is necessary to add some additive agents to the tablet in order to complement the formability of the tablet. However, the addition of additive agents may cause harmful effects to the tablet (e.g. enlarged size of the tablet), and thus some further improvement has been required.

In addition, when the inner core of press-coated tablets comprises powder/granular material with poor formability, the inner core has a very low hardness; thus the outer layer, which surrounds the inner core, needs a higher hardness than tablets without core (i.e. normal tablets) or typical press-coated tablets. It has been found in the course of completing the present invention.

The press-coated tablets disclosed in Patent References 1 and 2 are interesting as a novel technique for tablets. In particular, Patent Reference 2 discloses examples of preparations containing microcapsule-like granules in the inner core, and hence it was expected to apply the formulation to some functional formulations such as orally-disintegrating tablets. However, press-coated tablets with an outer layer similar to that of the formulation disclosed in Patent Reference 2 had a remarkably poor oral disintegrability (see, Comparative Examples 1 to 4 in the present invention). The inventors also found that some sufficient hardness were not achieved when press-coated tablets containing particles without formability were prepared by using the outer layers disclosed in Patent Reference 1 which is directed to a pressed-coated tablet undergoing quick disintegration (see, Comparative Examples 1 to 5 of the present invention).

As described above, in order to prepare a press-coated tablet with double-layered structure consisting of an inner core and an outer layer, in particular, a tablet containing particle without formability in its inner core, it is necessary to maintain the hardness of the tablet only with its outer layer and thus the outer layer of the tablet is required to be harder than a normal tablet. In case that the double-layered structure is applied to an orally disintegrating tablet, the hardness of the tablet had to be reduced so that the tablet can exhibit an adequate disintegrability. As a result, the conventional formulations and techniques of orally-disintegrating tablets could not be utilized without modification for providing a tablet with a desirable hardness and disintegrability, which are both required for a press-coated tablet having an inner core containing a powder/granular material with poor formability.

The purpose of the present invention is to newly develop a press-coated formulation characterized in that its inner core comprises a powder/granular material with poor formability, and provide a press-coated orally-disintegrating tablet with an excellent disintegrability and a suitable hardness as a whole tablet.

Solution to Problem

In general, it is difficult to prepare a tablet containing a large amount of particles without formability (e.g. functional particles), powders of an active ingredient and the like. In such a situation, the present inventors tried prepare a tablet in which its inner core comprises such particles or such powders and its outer layer surrounds the inner core. In preparing such press-coated tablet comprising a powder/granular material with poor formability as mentioned above, it was extremely difficult to achieve a suitable hardness as a whole tablet while maintaining an oral disintegrability. However, the present inventors have extensively studied and then have found that the above problem can be solved by using a combination of particular ingredients in the outer layer. That is, the present inventors have found that it is possible to prepare a press-coated orally-disintegrating tablet with an outer layer surrounding its inner core wherein the inner core comprises a powder/granular material with poor formability; the outer layer comprises microcrystalline cellulose, a sugar or a sugar alcohol and the below-defined particular ingredients (c); and the pressed tablet has a suitable hardness and disintegrability as a whole tablet. In more detail, the present invention provides a press-coated orally-disintegrating tablet wherein the inner core has a thickness in the range of 30 to 80% per that of the whole tablet, and the outer layer comprises (a) microcrystalline cellulose, (b) sugar or sugar alcohol, and (c) one or more particular ingredients selected from the group consisting of crospovidone, starches, low-substituted hydroxypropylcellulose and carmellose; and the pressed tablet has a sufficient hardness and an excellent disintegrability in the oral cavity even when the inner core has poor formability.

The present invention provides various embodiments as follows.

Term 1

A press-coated orally-disintegrating tablet with an outer layer surrounding an inner core wherein the inner core has a thickness in the range of 30 to 80% per that of the whole tablet; and the outer layer comprises (a) microcrystalline cellulose, (b) a sugar or a sugar alcohol, and (c) one or more particular ingredients selected from the group consisting of crospovidone, starches, low-substituted hydroxypropylcellulose and carmellose.

Term 2

The press-coated orally-disintegrating tablet of Term 1 wherein the inner core is a powder/granular material with poor formability.

Term 3

The press-coated orally-disintegrating tablet of Term 1 or 2 wherein the outer layer has a porosity of 1 to 20%.

Term 4

The press-coated orally-disintegrating tablet of any one of Terms 1 to 3 wherein the inner core has a porosity of 10 to 90%.

Term 5

The press-coated orally-disintegrating tablet of any one of Terms 1 to 4 wherein the microcrystalline cellulose (a) is contained in an amount of 10 to 90 wt % per 100 wt % of the outer layer.

Term 6

The press-coated orally-disintegrating tablet of any one of Terms 1 to 5 wherein the particular ingredient(s) (c) comprises starches, and the starches are contained in an amount of 3 to 40 wt % per 100 wt % of the outer layer.

Term 7

The press-coated orally-disintegrating tablet of any one of Terms 1 to 5 wherein the particular ingredient(s) (c) comprises one or more ingredients selected from the group consisting of crospovidone, low-substituted hydroxypropylcellulose and carmellose; and the particular ingredient(s) (c) in total is contained in an amount of 3 to 20 wt % per 100 wt % of the outer layer.

Term 8

The press-coated orally-disintegrating tablet of any one of Terms 1 to 7 wherein the sugar or sugar alcohol (b) comprises mannitol.

Term 9
   The press-coated orally-disintegrating tablet of any one of Terms 1 to 6 and 8 wherein the particular ingredient(s) (c) comprises corn starch.
Term 10
   The press-coated orally-disintegrating tablet of any one of Terms 1 to 9 wherein the inner core has a thickness in the range of 30 to 70% per that of the whole tablet.
Term 11
   The press-coated orally-disintegrating tablet of any one of Terms 1 to 10 wherein the porosity of the inner core is greater than that of the outer layer.
Term 12
   The press-coated orally-disintegrating tablet of any one of Terms 1 to 11 wherein the inner core comprises an active ingredient.

Effect of Invention

The present invention can provide a press-coated orally-disintegrating tablet characterized by an inner core comprising a powder/granular material with poor formability, which has an excellent disintegrability and a suitable hardness as a whole tablet.

BEST MODE FOR CARRYING OUT INVENTION

The press-coated orally-disintegrating tablet of the present invention composes of an "inner core" which comprises a powder/granular material with poor formability such as a microcapsule-like functional particle, and an "outer layer" which surrounds the inner core to give suitable hardness and disintegrability to the formed tablet.

Also, the present invention can be applied to a powder with poor formability, a granulated material with poor formability or a powder/granular material with poor formability besides a microcapsule-like functional particle in its inner core to provide a tablet having sufficient hardness and disintegrability.

In the present invention, the "outer layer" comprises (a) microcrystalline cellulose, (b) a sugar or a sugar alcohol, and (c) one or more particular ingredients selected from the group consisting of crospovidone, starches, low-substituted hydroxypropylcellulose and carmellose. Using the combination of these ingredients, it becomes possible to prepare a press-coated orally-disintegrating tablet with a sufficient hardness and an excellent disintegrability as a final formulation, even when the inner core comprises ingredients with poor formability. The inner core, which is a powder/granular material with poor formability, preferably has a thickness in the range of 30% or more per that of the whole tablet to produce a good disintegrability.

The "orally disintegrating tablet" used herein means a tablet which rapidly disintegrates in the oral cavity without water. Oral disintegration time of the "orally disintegrating tablet" can be measured using a disintegration test in the human oral-cavity or in a device. An orally disintegrating tablet tester used herein is, for example, ODT-101 (manufactured by Toyama Sangyo Co., Ltd.). The oral disintegrating tablet used herein means a tablet whose inner core and outer layer are disintegrated or dispersed in a disintegration time of typically 60 seconds or less, preferably 45 seconds or less, more preferably 30 seconds or less, and most preferably 20 seconds or less. In the actual disintegration test in the human oral cavity, the time from putting a tablet into the oral cavity to the complete oral disintegration was measured as the oral disintegration time. After the tests, the recipients took out the test sample from their oral cavity and washed their oral cavity with clean water.

The value of mean particle size used herein was measured with, for example, a laser diffraction particle size analyzer manufactured by SYMPATEC (HELOS & RODOS) or manufactured by Shimadzu (SALD 3000).

The value of bulk density used herein was measured using Constant Mass Method (Method 1) as described in the Japanese Pharmacopoeia 15th Edition. In specific, the value is calculated according to the formula below wherein $X$ cm$^3$ represents a bulk volume when putting typically about 30 g of the sample into a 100 mL (cm$^3$) graduated glass cylinder without consolidation; provided that if the sample spills out of the cylinder, the mass of the sample is optionally reduced.

Bulk Density (g/cm$^3$)=Mass of Sample (g)/$X$ (cm$^3$)

The tablet hardness of the present invention was given by measuring the force required for diametrically crushing the tablet using a tablet hardness tester (PORTABLE CHECKER PC-30, manufactured by Okada Seiko Co., Ltd.). The "absolute hardness" was calculated using the obtained tablet hardness according to the following formula. The "absolute hardness" is a value obtained by dividing the hardness measured with the tablet hardness tester by the longitudinal sectional area (tablet diameter (mm)×tablet thickness (mm)).

The absolute hardness (N/mm$^2$)=the hardness (N)/the longitudinal sectional area (mm$^2$).

The term "with suitable hardness and disintegrability" used herein means that the balance of the absolute hardness and the orally-disintegrating time is good. As an index of the balance thereof, the term "HDBI (Hardness and Disintegrating Balance Index)" is defined according to the formula below. The larger value means the better balance of the hardness and the disintegrability. In detail, the orally-disintegrating tablet of the present invention has the HDBI value of 0.15 or more, and preferably 0.2 or more. The calculated value of HDBI is likely to vary in case that the oral disintegration time is too slow or the absolute hardness is too low, and hence it is desirable to keep the oral disintegration time to 60 seconds or less and the absolute hardness to 1 N/mm$^2$ or more by adjusting the compressing pressure.

HDBI (N/mm$^2$·sec)=the absolute hardness (N/mm$^2$)/the oral disintegration time (sec)

Generally, the porosity can be calculated according to the following formula:

The porosity of the tablet (%)=(1−$Wt$/($\rho$×$V$))×100

$\rho$: the true density of the tablet (mg/mm$^3$),
$V$: the volume of the tablet (mm$^3$),
$Wt$: the weight of the tablet (mg).

The porosity can be measured as a void ratio with, for example, a pore distribution analyzer manufactured by Shimadzu (Micromeritics).

In the present invention, the porosity of the outer layer can be calculated according to the following formula:

The porosity of the outer layer (%)=(1−$Wt$/($\rho$×3.14×$D^2$×$T$))×100

$\rho$: the true density of the outer layer (mg/mm$^3$),
$D$: the radius of the outer layer (under-portion) (mm),
$T$: the thickness of the outer layer (under-portion) (mm),
$Wt$: the weight of the outer layer (under-portion) (mg).

In the present invention, the thickness of the inner core was calculated as described below. The thickness of the whole tablet was measured by a digital caliper (manufactured by Mitutoyo Co., Ltd.). The press-coated tablet was diametrically divided, the cross sectional surface was analyzed using a digital microscope (VHX-500, manufactured by Keyence Co., Ltd.), and the thicknesses of the upper portion and the under portion of the outer layer were measured.

The thickness of the inner core (mm)=the thickness of the whole tablet (mm)−the sum (mm) of thicknesses of the upper and under portions in the outer layer In the present invention, the term "ratio of the thickness of the inner core" means a ratio of the thickness of the inner core per the thickness of the whole tablet, i.e., the ratio of the thickness of the inner core in the cross sectional area parallel for the side of the tablet. In case that the ratio of the thickness of the inner core depends on the divided site, the highest ratio among the entire cross sectional surfaces is defined as "the ratio of the thickness of the inner core".

The ratio of the thickness of the inner core (%)=the thickness of the inner core (mm)/the thickness of the whole tablet (mm)×100

In the present invention, the porosity of the outer layer is preferably lowered to increase the hardness compared with a general tablet without an inner core. The outer layer has a porosity of typically 1 to 20%, and preferably 1 to 15%. The inner core has a porosity of typically 10 to 90%, and preferably 20 to 80%. Typically, it is preferable that the porosity of the inner core is greater than that of the outer layer.

The present invention is further illustrated in the followings.

(1) Outer Layer (a) Microcrystalline Cellulose

Microcrystalline cellulose used herein as an essential ingredient for the outer layer is not limited to any specific one as long as it can be orally administered. A preferred mean particle size of microcrystalline cellulose used as a starting material is 150 µm or less, more preferably 130 µm or less, and even more preferably 120 µm or less from the aspect of the feeling in the oral cavity because a formulation prepared by using microcrystalline cellulose with a large mean particle size brings sandy feeling in the oral cavity after oral disintegration.

In the present press-coated orally-disintegrating tablet, the outer layer alone needs to provide a sufficient hardness for the whole tablet. However, the hardness of tablet is not sufficient when the outer layer has a low content of microcrystalline cellulose, and thus the microcrystalline cellulose used herein is contained in an amount of typically 10 wt % or more per 100 wt % of the whole weight of the outer layer. On the other hand, from the viewpoint of the feeling in the oral cavity, the tablet makes a powdery feeling when the content of microcrystalline cellulose is too high, and thus the content thereof used herein is typically 90 wt % or less per 100 wt % of the whole weight of the outer layer. Considering the balance of the tablet hardness and the disintegration time, the content of microcrystalline cellulose is 10 to 90 wt a, and preferably 20 to 70 wt % per 100 wt % of the whole weight of the outer layer. The microcrystalline cellulose used herein includes, for example, CEOLUS™ (PH-101, PH-102, PH-301, PH-302, PH-F20J, KG-802, KG-1000, ST-02: manufactured by Asahi Kasei Chemicals Co., Ltd.) and AVICEL™ (PH-101, PH-102, PH-301, PH-302, FD-101, FD-301, FD-F20: manufactured by FMC BioPolymer Co., Ltd). The microcrystalline cellulose used herein may be any one type of them or a combination of two or more types thereof.

The microcrystalline cellulose used herein has a bulk density of preferably 0.1 g/cm$^3$ to 0.5 g/cm$^3$, and more preferably 0.1 g/cm$^3$ to 0.3 g/cm$^3$. The microcrystalline celluloses with a bulk density of 0.1 g/cm$^3$ to 0.3 g/cm$^3$ include, for example, CEOLUS KG-802 and KG-1000.

(b) Sugar or Sugar Alcohol

A sugar or sugar alcohol used herein as an essential ingredient for the outer layer is not limited to any specific one as long as it can be administered orally; and may include both natural products derived from animals or plants, and artificial products manufactured through a chemical synthesis or a fermentation process. The sugar or sugar alcohol used herein is contained in an amount of typically 0.5 to 84 wt %, preferably 20 to 80 wt %, and more preferably 20 to 75 wt % per 100 wt % of the whole weight of the outer layer in terms of the feeling in the oral cavity.

The sugar used herein includes, for example, glucose, fructose, sucrose, lactose, maltose, trehalose, and palatinose; and from the viewpoint of the balance of the tablet hardness and disintegrability, lactose and trehalose are preferable, and lactose is the most preferable. The sugar alcohol used herein includes, for example, erythritol, mannitol, xylitol, sorbitol, and maltitol; and preferably erythritol and mannitol. The most preferred sugar alcohol is mannitol from the viewpoint of the balance of the tablet hardness and disintegrability.

The lactose used herein for the outer layer is not specifically limited as long as it can be administered orally; and includes α-lactose monohydrate, anhydrous β-lactose, and anhydrous α-lactose. Among them, α-lactose monohydrate is preferable from the aspect of ease in handling. Furthermore, from the viewpoint of feeling in the oral cavity, the lactose used as a starting material has a mean particle size of preferably 150 µm or less, and more preferably 120 µm or less.

The mannitol used herein for the outer layer is not specifically limited as long as it can be administered orally, and it is preferably D-mannitol. The crystal form of mannitol used herein is not specifically limited, and it may be α-, β- or δ-form, or it may an amorphous form obtained by using a spray-drying technique. Alternatively, the mannitol used herein may have a spherical shape and a high density as disclosed in, for example, JP 11 (1999)-092403 A. The mannitol used herein has a mean particle size of preferably 10 µm to 300 µm, more preferably 10 µm to 250 µm, and even more preferably 30 µm to 200 µm, but it is not specifically limited thereto. In order to achieve the desired particle size, the mannitol may be optionally milled with, for example, an airflow mill and a hammer mill.

In view of the feeling in the oral cavity, the most preferable sugar or sugar alcohol is mannitol. The sugar or sugar alcohol may be used alone or in combination with two or more thereof, depending on the desirable formulation.

(c) Particular Ingredients

The particular ingredients used herein as an essential ingredient for the outer layer are characterized as at least one ingredient selected from the group consisting of crospovidone, starches, low-substituted hydroxypropyl-cellulose and carmellose. A press-coated orally-disintegrating tablet without the particular ingredient (described below) or a press-coated orally-disintegrating tablet with an ingredient for increasing the disintegrability other than the above particular ingredient cannot have the desired effects because the porosity of the outer layer of the press-coated orally-disintegrating tablet need to be lowered to increase the hardness of the outer layer compared with a normal tablet without an inner core. In contrast, the present inventors have found that the desired effects can be achieved when the outer layer comprises the particular ingredient in combination with microcrystalline cellulose and a sugar or a sugar alcohol.

(c-1) Crospovidone

Crospovidone used herein may be typically a crospovidone adapted to the Japanese Pharmacopoeia, but it should not be limited thereto. A preferred mean particle size of crospovidone used as a starting material is, but not limited to, preferably 10 µm to 200 µm, more preferably 10 µm to 150 µm, and even more preferably 10 µm to 100 µm from the aspect of the feeling in the oral cavity because a formulation prepared by using crospovidone with a large mean particle size brings sandy feeling in the oral cavity after oral disintegration. In order to achieve the desired particle size, crospovidone may be optionally milled with, for example, an airflow mill and a hammer mill. The crospovidone is contained in an amount of typically 3 to 20 wt % and preferably 5 to 10 wt % per 100 wt % of the whole weight of the outer layer.

(c-2) Starches

Starches used herein may include, for example, corn starch, potato starch, rice starch, wheat starch, sweet potato starch, mung bean starch, tapioca starch and partly pregelatinized starch; and corn starch is preferable among them. In the present invention, completely-pregelatinized starch cannot be applied due to its poor disintegrability. These starches used herein may be any one type of them or a combination of two or more types thereof. The mean particle size of starches is, but not limited to, preferably 10 µm to 200 µm, more preferably 10 µm to 100 µm, and even more preferably 10 µm to 50 µm, from the aspect of the feeling in the oral cavity because a formulation prepared by using starches with a large mean particle size brings sandy feeling in the oral cavity after oral disintegration. In order to achieve the desired particle size, starches may be optionally milled with, for example, an airflow mill and a hammer mill. From the aspect of the hardness and the disintegrating time, the total amount of the starches used herein is typically 3 to 40 wt % and preferably 20 to 40 wt % per 100 wt % of the outer layer.

(c-3) Low-Substituted Hydroxypropylcellulose (L-HPC)

The degree of substitution in low substituted hydroxypropylcellulose of the present invention is not limited as long as it is adapted to the Japanese Pharmacopoeia, and generally the degree is in the range of 7.0 to 12.9%. The mean particle size of low substituted hydroxypropylcellulose used as a starting material is, but not limited to, preferably a range of 10 µm to 200 µm, more preferably 10 to 150 µm, even more preferably 10 µm to 100 µm from the aspect of the feeling in the oral cavity because a formulation prepared by using low substituted hydroxypropylcellulose with a large mean particle size brings sandy feeling in the oral cavity after oral disintegration. In order to achieve the desired particle size, low substituted hydroxypropylcellulose may be optionally milled with, for example, an airflow mill and a hammer mill. The low-substituted hydroxypropylcellulose is contained in an amount of typically 3 to 20 wt % and preferably 5 to 10 wt % per 100 wt % of the whole weight of the outer layer.

(c-4) Carmellose (CMC)

Carmellose used herein is not specifically limited, but carmellose adapted to the Japanese Pharmacopoeia may be used herein. The mean particle size of carmellose used as a starting material is, but not limited to, preferably a range of 10 µm to 200 µm, more preferably 10 µm to 150 µm, and even more preferably 10 µm to 100 µm from the aspect of the feeling in the oral cavity because a formulation prepared by using carmellose with a large mean particle size brings sandy feeling in the oral cavity after oral disintegration. In order to achieve the desired particle size, carmellose may be optionally milled with, for example, an airflow mill and a hammer mill. The carmellose is contained in an amount of typically 3 to 20 wt % and preferably 5 to 10 wt % per 100 wt % of the whole weight of the outer layer.

Among the particular ingredients described above, preferred examples thereof include crospovidone, starches and low substituted hydroxypropylcellulose; more preferably crospovidone and starches; and even more preferably crospovidone and corn starch. From the aspect of the balance of the hardness and disintegrability, the most preferred example of the particular ingredients is crospovidone. Incase that the particular ingredients used herein comprise starches and one or more particular ingredients, the total amount of the particular ingredients is typically 6 to 43 wt % and preferably 25 to 40 wt % per 100 wt % of the whole weight of the outer layer. In case that the above-mentioned particular ingredients other than starches are composed of two or more ingredients, the total amount of the particular ingredients other than starches is typically 6 to 20 wt %, and preferably 6 to 10 wt % per 100 wt % of the whole weight of the outer layer.

Additional Formulation Ingredients

Additional formulation ingredients can be added to the outer layer of the present orally-disintegrating tablet besides the ingredients described above. With regard to the "additional formulation ingredients" in the invention, any formulation ingredients can be used herein as long as the ingredients give no or little influence on the hardness and the disintegrating time of the tablet without any trouble on formulation. The additional ingredients used herein include, for example, other fillers, disintegrants, binders, sweetening agents, taste correctives/odor correctives, stabilizers, surfactants, fluidizing agents, antistatic agents, coating agents, lubricants, colorants, flavors and the like. The "additional formulation ingredients" are contained in an amount of 0.01 to 25 wt % per 100 wt % of the outer layer.

Lubricant

In the present invention, it is preferable that the tablet comprises a lubricant in the above additional formulation ingredients in its outer layer. The lubricant includes, for example, stearic acid, metallic stearate, sodium stearyl fumarate, sucrose ester of fatty acid, talc, hydrogenated oil, and macrogol. The metallic stearate includes, for example, magnesium stearate, calcium stearate aluminum stearate and the like. The lubricant used herein preferably includes stearic acid and metallic stearate, especially magnesium stearate in terms of ease of manufacture. On the other hand, sodium stearyl fumarate is preferable from the viewpoint of the balance of the hardness and disintegrability as well as the ease of manufacture. The mean particle size of lubricant before the formulation process is in the range of 0.5 µm to 50 µm and preferably 1 µm to 30 µm. The lubricant is contained in an amount of typically 0.01 to 2.5 wt %, preferably 0.01 to 2 wt %, and more preferably 0.01 to 1 wt % per 100 wt % of the outer layer. In the present invention, the lubricant can be added to the formulation either by external lubricating methods or internal lubricating methods.

(2) Inner Core

In the present invention, the inner core is not limited to any specific one as long as the inner core has a good oral disintegration and dispersibility. The outer layer of the present invention can give a sufficient hardness to the whole tablet even when the inner core of the tablet has a poor formability, thus the present invention is also effective for a tablet containing the inner core comprising a "powder/granular material with poor formability". The "powder/granular material with poor formability" means a powder/granular material containing a powder and/or a granulated material with poor formability; and it also intends that it is impossible to give a pressed substance or a pressed substance with an extremely low hardness even if the compression succeeds. In detail, it means that when the substance (50 mg) is compressed into tablet (diameter 6 mm) at a pressure of 4 kN, a pressed substance cannot be obtained or a pressed substance with an extremely low hardness (10 N or less) is obtained even if the compression succeeds. The mean particle size of the "powder/granular material with poor formability" used herein is, but not limited to, generally 3 mm or less, preferably 1 mm or less from the aspect of the feeling in the oral cavity, even more preferably 300 μm or less, and the most preferably 150 μm or less. In the present invention, it is preferable that the inner core comprises an active ingredient, for example, including functional particle (such as small capsule and coated granule) containing an active ingredient; powder of an active ingredient; or mixed powders or granulated material which is prepared by adding additives to the said functional particle (such as small capsule and coated granule) containing an active ingredient, or powder of an active ingredient to improve the fluidity, the dispersibility and the adherability.

The said granulated material may be prepared by, for example, a fluidized bed granulation, an extrusion method, a dry-process compression and granulating method, a rotor granulation method, a rotor fluidized-bed granulation method, a high-speed mixer granulating method, and a fracturing granulation method.

The functional particles comprising an active ingredient can be prepared according to the procedures described in, for example, JP 3 (1991)-130214 A, JP 2007-063263 A, WO 2005/055989, and JP 2002-332226 A. In detail, a small capsule among the functional particles includes, for example, microcapsules in the broad sense of the term, such as microcapsules, seamless capsules, mini soft capsules, and microspheres.

A coated granule among the functional particle includes, for example, polymer-coated granules, wax-coated granules, and sugar-coated granules. It also includes a particle which might be inactivated by a high-pressure tableting, such as enzyme-containing granules. The various coated particles described above include, for example, granules prepared by coating granular particles with coating layer, granules comprising a core in their granular particles, and granules prepared by coating granular particles comprising a core in their granular particles with coating layer; which are designed to improve the sustained release, enteric solubility, gastric solubility, heat resistance, light resistance, stability or bitter taste. In the present invention, the term "coated" or "coating" includes covering the whole or a part of the surface of an active ingredient with a coating material. As apparatuses for this coating, ordinary fluidized-bed granulating machine (including rotor fluidized-bed granulating machine, Wurster fluidized-bed granulating machine and the like) can be mentioned; and in order to suppress particle coarsening in the step, preference is given to improved Wurster fluidized-bed granulating machines equipped with an apparatus for forced circulation from side (for example, SPC, manufactured by POWREX CORPORATION, and the like), hybrid fluidized-bed granulating machines equipped with a grinding mechanism (screen impeller type, blade stator type, cross-screws, lump breakers and the like) (for example, super fine particle coating and granulating processor SFP-01, manufactured by POWREX CORPORATION, and the like), and rotary fluidized-bed granulating machines (for example, OMNITECS, manufactured by NARA MACHINERY CO. LTD., and the like). As apparatuses for spray drying, ordinary spray dryers (manufactured by OKAWARA CORPORATION, manufactured by OHKAWARA KAKOKI CO. LTD., manufactured by Yamato, manufactured by Niro, and the like) can be used.

The material of the inner core used for the preparation of the functional particles described above includes, for example, commercially available microcrystalline cellulose spheres, sucrose-starch spherical granules, purified sucrose spherical granules, lactose-crystalline cellulose spherical granules, D-mannitol, dibasic calcium phosphate anhydrate, magnesium oxide, magnesium hydroxide and the like.

Active Ingredient

The active ingredient used in the orally-disintegrating tablet of the present invention is not limited to any specific one as long as the active ingredient is served as a pharmaceutical active ingredient for the treatment and the prevention of diseases and is orally administrable. The active ingredient includes, for example, alimentary roborants; antipyretic analgesic antiphlogistics; psychotropic agents; hypnotics; antispasmodics; central nervous system acting drugs; cerebral metabolism improving agents; cerebral circulation improving agents; antiepileptics; sympathomimetics; digestants; antiulcer agents; prokinetic agents; antacids; antitussive expectorants; antimotility agents; antiemetics; respiratory stimulants; bronchodilators; antiallergic agents; cardiacs; antiarrhythmic agents; diuretics; vasoconstrictor; coronary vasodilators; vasodilator agents; peripheral vasodilators; antihyperlipemic drugs; cholagogues; chemotherapeutics; drugs for diabetic complications; osteoporosis treating drugs; antirheumatics; skeletal muscle relaxants; gout suppressant; anticoagulants; antineoplastic agents and the like. The active ingredient used herein may be in a salt thereof or in a free form as long as it is pharmaceutically acceptable. Also, it may be in form of a solvate such as alcoholate, and hydrate. Furthermore, the above-mentioned active ingredients may be used alone or in a combination of two or more types thereof.

When the inner core in the present invention comprises an active ingredient, the content of the active ingredient in the inner core is, but not specifically limited to, 0.1 to 100 wt % and preferably 1 to 95 wt % per 100 wt % of the inner core. The "content of an active ingredient in the inner core" in the present invention is based on a form of a "pharmaceutical active ingredient" generally employed as a drug, i.e., in case of a drug in a salt form, it is based on the amount of the salt. Also, the above active ingredient can be added to the outer layer to the extent to have no or little action on the hardness and the oral disintegration time of the final formulation.

(3) Process of Press-Coated Orally-Disintegrating Tablet

The press-coated orally-disintegrating tablet of the present invention can be prepared using a known tableting machine capable of preparing a press-coated formulation. A press-coated orally-disintegrating tablet containing a large amount of microcapsule-like functional particle in its inner core can be prepared using a tableting machine for press-coated formulation disclosed in WO 2005/097041, etc., or a similar tableting machine or method for a preparation of press-coated formulation with a poor formable inner core.

The laboratory procedure of the present press-coated orally-disintegrating tablet includes the following:

A mixture of the ingredients (a) to (c) described above is placed in a die whose diameter corresponds to that of the desired inner core, and the die is gently shaken to smooth the surface of the powder (which is the under-portion of the outer layer). On the mixture, a suitable amount of a powder/granular material with poor formability as an ingredient for the inner core is put, and the layered material is temporarily pressed at a relatively low pressure using a hand press machine. This temporarily-pressed substance is placed on a punch whose diameter corresponds to that of the final formulation concentrically in a manner to make the under-portion of the outer layer placed downward. A die is covered thereon, and a suitable amount of the additional above-mentioned mixture of the ingredients of the outer layer (for the side- and upper-portions of the outer layer) is put on the temporarily-pressed substance. The composition between the die and the punch is finally pressed into tablet to prepare a press-coated orally-disintegrating tablet.

Another example of the procedure includes the following:

A mixture of the ingredients (a) to (c) described above is placed in a die whose diameter corresponds to that of the desired tablet and temporarily pressed at a relatively low pressure using a hand press machine. Additionally, a power/granular material with poor formability as an ingredient for the inner core is placed in a die whose diameter corresponds to that of the inner core and temporarily pressed at a relatively low pressure using a hand press machine. The temporarily-pressed substance for the inner core is placed concentrically on the temporarily-pressed material for the outer layer described above. A die is covered thereon, and a suitable amount of the additional above-mentioned mixture of the ingredients of the outer layer is put on the temporarily-pressed substance. The composition between the die and the punch is finally pressed into tablet to prepare a press-coated orally-disintegrating tablet.

The material of the outer layer may be prepared as a granule before tableting according to a known method in the art. For example, a press-coated formulation may be prepared using a homogenous mixture of the above ingredients (a) to (c) according to the method described above. Also, each ingredient of above (a) to (c) is granulated prior to the tableting, a lubricant is added to a mixture of the granulated ingredients, and then a press-coated formulation may be prepared using the obtained mixture according to the method described above. Furthermore, portions of each ingredient of above (a) to (c) are granulated prior to the tableting, the rest of the ingredients of (a) to (c) and a lubricant were added to a mixture of the granulated ingredients, and then a press-coated formulation may be prepared using the obtained mixture according to the method described above. The granulating method includes, for example, a fluidized bed granulation, an extrusion method, a dry-process compression and granulating method, a rotor granulation method, a rotor fluidized-bed granulation method, a high-speed mixing/granulating method, and a fracturing granulation method.

(4) Press-Coated Orally-Disintegrating Tablet

The press-coated orally-disintegrating tablet prepared as described above means a formulation which is administrable without water and shows a rapid disintegration in the oral cavity. In detail, the orally-disintegrating tablet of the present invention means a formulation which is orally disintegrated mainly by saliva within approximately 60 seconds, typically 43 seconds, preferably 30 seconds, and more preferably 20 seconds.

Furthermore, the present orally-disintegrating tablet has a sufficient hardness to avoid being chipped or cracked in manufacturing process, transportation, or clinical practice. In case that several drugs are administered to patients, in order to improve the drug compliance these days, hospitals or dispensing pharmacies often provide all-in-one packages wherein each package contains the several medicaments per every administration time to prevent the patients from forgetting to take the medicaments or making a mistake of dosing. In order to handle tablets in such a manner, it is also desirable that the tablets have sufficient hardness to avoid being chipped or cracked. In particular, the present orally-disintegrating tablet has a double-layered structure which causes the tablet to be chipped or cracked more easily than typical orally-disintegrating tablets, and hence it is desirable that the present tablet is harder than typical tablets. Specifically, the present orally-disintegrating tablet has an absolute hardness of 2.0 N/mm$^2$ or more, and preferably 2.5 N/mm$^2$ or more.

The shape of the press-coated orally-disintegrating tablet which is the final formulation of the present invention may be, but not specifically limited to, a round-shaped tablet, a round-shaped R-tablet, a round-shaped tablet with angular corners, various irregular-shaped tablets and the like. The diameters of the round-shaped tablet, the round-shaped R-tablet, and the round-shaped beveled edge tablet of the present invention are generally 5 mm to 16 mm, and preferably 7 mm to 10 mm.

In the present invention, the "ratio of the thickness of the inner core" is generally 30 to 80%, preferably 30 to 70%, and more preferably 30 to 60%. The thickness of the outer layer used herein is generally 0.5 mm to 2.0 mm, preferably 0.5 mm to 1.5 mm, and more preferably 0.5 mm to 1.0 mm.

In the present invention, the percentage of the volume of the inner core per 100% of the final formulation is 10 to 60% and preferably 15 to 50%.

The press-coated orally-disintegrating tablet of the present invention should satisfy disintegrability in the oral cavity and sufficient hardness to maintain its form as a formulation when handling in manufacturing processes, distribution processes, clinical practices and the like. The outer layer is required to have a sufficient hardness because the present invention is characterized in that the formulation of the present invention contains a powder/granular material with poor formability as its inner core. In addition, the higher hardness of the outer layer is required compared with that of a conventional orally-disintegrating tablet without a core. The lower porosity of the outer layer is preferable compared with that of a conventional tablet so that the sufficient hardness can be achieved. The outer layer of the tablet has a porosity of preferably 1 to 20% and more preferably 1 to 15%.

EXAMPLE

Hereinafter, the present invention is further illustrated with the following examples, but should not be construed to be limited thereto.

Unless otherwise noted, mannitol; lactose; sodium stearyl fumarate; corn starch; magnesium stearate; carmellose; low-substituted hydroxypropylcellulose (L-HPC); micro-crystalline cellulose spheres; microcrystalline cellulose and crospovidone used in Examples are as follows:

mannitol (Pearlitol 50C: manufactured by ROQUETTE);

lactose hydrate (Pharmatose 200M: manufactured by DMV International);

sodium stearyl fumarate (PRUV: manufactured by Kimura Sangyo Co., Ltd);

corn starch [(XX16) W: manufactured by Nihon Shokuhin Kako Co., Ltd];

magnesium stearate (light and vegetative: manufactured by Taihei Chemical Industrial Co., Ltd.);

carmellose (NS-300: manufactured by Gotoku Chemical Co., Ltd.);

low-substituted hydroxypropylcellulose (LH-21: manufactured by Shin-Etsu Chemical Co., Ltd.);

microcrystalline cellulose spheres (CELPHERE® CP-203: manufactured by Asahi KASEI Chemicals Co., Ltd.);

microcrystalline cellulose (CEOLUS® PH-101 or CEOLUS® PH-301, CEOLUS® KG-802, CEOLUS® KG-1000: all manufactured by Asahi KASEI Chemicals Co., Ltd.); and crospovidone (KOLLIDON® CL: manufactured by BASF Japan Ltd., or Polyplasdone XL-10: manufactured by ISP Japan Ltd.).

Examples 1-1 to 1-5

Study of the Particular Ingredients

<Preparation of Press-Coated Orally-Disintegrating Tablets>

Five types of formulations were prepared according to the formulae shown in Table 1-1, wherein each particular ingredient in the outer layer is different from each other. Firstly, the ingredients of each outer layer were mixed. A portion of each mixture (40 mg) was placed in a die (6 mm diameter), and the die was gently shaken to smooth the surface of the powder (which is the under-portion of the outer layer). On the mixture, 50 mg of microcrystalline cellulose spheres (CELPHERE, CP-203) as an ingredient for the inner core was put, and then the layered material was temporarily pressed at a low pressure (3 kN) using a hand press machine (oil hydraulic press system, manufactured by RIKEN). This temporarily-pressed substance was placed on a punch (8 mm diameter) concentrically in a manner to make the under-portion of the outer layer placed downward. A die (8 mm diameter) was covered thereon, and the additional above-mentioned mixture of the ingredients of the outer layer (for the side- and upper-portions of the outer layer, 140 mg) was put on the temporarily-pressed substance. The composition between the punch and the die was finally pressed at a pressure of 15 kN in Examples 1-2 and 1-5, and 10 kN in the other Examples to prepare the desired press-coated orally-disintegrating tablets. In addition, the hardness of a pressed tablet (50 mg) prepared by pressing only the microcrystalline cellulose spheres (CELPHERE CP-203) used herein at a pressure of 4 kN in a punch/die (6 mm diameter) was less than 10 N.

TABLE 1-1

| | | Formula (mg) | | | | |
|---|---|---|---|---|---|---|
| | | Ex. 1-1 | Ex. 1-2 | Ex. 1-3 | Ex. 1-4 | Ex. 1-5 |
| Inner core | Microcrystalline cellulose spheres (CELPHERE CP-203) | 50.0 | 50.0 | 50.0 | 50.0 | 50.0 |
| Outer layer | D-Mannitol | 131.4 | 131.4 | 131.4 | 131.4 | — |
| | Lactose | — | — | — | — | 131.4 |
| | Corn starch | 9.0 | — | — | — | — |
| | Crospovidone | — | 9.0 | — | — | 9.0 |
| | Carmellose | — | — | 9.0 | — | — |
| | L-HPC (LH-21) | — | — | — | 9.0 | — |
| | Microcrystalline cellulose (KG-802) | 36.0 | 36.0 | 36.0 | 36.0 | 36.0 |
| | Na-stearylfumarate | 3.6 | 3.6 | 3.6 | 3.6 | 3.6 |
| | Total | 230.0 | 230.0 | 230.0 | 230.0 | 230.0 |

TABLE 1-2

| | | Formulation ratio in the outer layer (wt %) | | | | |
|---|---|---|---|---|---|---|
| | | Ex. 1-1 | Ex. 1-2 | Ex. 1-3 | Ex. 1-4 | Ex. 1-5 |
| Outer layer | D-Mannitol | 73.0 | 73.0 | 73.0 | 73.0 | — |
| | Lactose | — | — | — | — | 73.0 |
| | Corn starch | 5.0 | — | — | — | — |
| | Crospovidone | — | 5.0 | — | — | 5.0 |
| | Carmellose | — | — | 5.0 | — | — |
| | L-HPC (LH-21) | — | — | — | 5.0 | — |

TABLE 1-2-continued

| | Formulation ratio in the outer layer (wt %) | | | | |
|---|---|---|---|---|---|
| | Ex. 1-1 | Ex. 1-2 | Ex. 1-3 | Ex. 1-4 | Ex. 1-5 |
| Microcrystalline Cellulose (KG-802) | 20.0 | 20.0 | 20.0 | 20.0 | 20.0 |
| Na-stearylfumarate | 2.0 | 2.0 | 2.0 | 2.0 | 2.0 |
| Total | 100.0 | 100.0 | 100.0 | 100.0 | 100.0 |

The oral disintegration time, hardness, and thickness of the product tablets were measured; and the absolute hardness and HDBI thereof were calculated. The results are tabulated in Table 1-3 to show the physical properties of the product tablets. Tablets prepared in Examples 1-1 to 1-4 which comprise any one of carmellose, corn starch, L-HPC or crospovidone in their outer layer attained the oral disintegration time of 30 seconds or less, the absolute hardness of 2.0 N/mm$^2$ or more, and a high value of HDBI which is an index of the balance of the hardness and disintegrability. Furthermore, all the formulations had a good feeling without dryness in the oral cavity. In all these formulations, the measured porosity of the under-portion of the outer layer was 20% or less. The value of HDBI was the highest in the case that the formulation comprised crospovidone as the particular ingredient (Example 1-2). Moreover, even when the mannitol used in Example 1-2 was replaced with lactose as in Example 1-5, the tablet of Example 1-5 similarly attained the oral disintegration time of 30 seconds or less, the absolute hardness of 2.0 N/mm$^2$ or more, and a high value of HDBI which is an index of the balance of the hardness and disintegrability.

TABLE 1-3

| | Physical properties of the tablets | | | | |
|---|---|---|---|---|---|
| | Ex. 1-1 | Ex. 1-2 | Ex. 1-3 | Ex. 1-4 | Ex. 1-5 |
| Orally-disintegrating time (sec) | 14 | 14 | 15 | 15 | 17 |
| Absolute hardness (N/mm$^2$) | 2.1 | 2.9 | 2.2 | 2.4 | 3.9 |
| HDBI | 0.15 | 0.21 | 0.15 | 0.16 | 0.23 |

Comparative Examples 1-1 to 1-3

Tablets without the Particular Ingredients or Microcrystalline Cellulose (Case 1)

Several formulations were prepared in the same manner as Example 1-1 according to the formulae shown in Table 2-1, wherein their outer layers lack either the particular ingredients or microcrystalline cellulose. The mannitol used herein was Mannite S (manufactured by Towa Kasei Co., Ltd.). The final compression into tablet was carried out at a pressure of 4 kN and 15 kN in Comparative Examples 1-1 and 1-2, and 15 kN in Comparative Example 1-3.

TABLE 2-1

| | | Formula (mg) | | |
|---|---|---|---|---|
| | | Comp. Ex. 1-1 | Comp. Ex. 1-2 | Comp. Ex. 1-3 |
| Inner core | Microcrystalline cellulose spheres (CELPHERE CP-203) | 50.0 | 50.0 | 50.0 |

TABLE 2-1-continued

| | | Formula (mg) | | |
|---|---|---|---|---|
| | | Comp. Ex. 1-1 | Comp. Ex. 1-2 | Comp. Ex. 1-3 |
| Outer layer | Lactose | 45.0 | — | — |
| | D-Mannitol | — | 45.0 | 159.7 |
| | Corn starch | — | — | 16.7 |
| | Microcrystalline cellulose (PH-102) | 133.9 | 133.9 | — |
| | Mg-stearate | 1.1 | 1.1 | — |
| | Na-stearyl fumarate | — | — | 3.6 |
| | Total | 230.0 | 230.0 | 230.0 |

TABLE 2-2

| | | Formulation ratio in the outer layer (wt %) | | |
|---|---|---|---|---|
| | | Comp. Ex. 1-1 | Comp. Ex. 1-2 | Comp. Ex. 1-3 |
| Outer layer | Lactose | 25.0 | — | — |
| | D-Mannitol | — | 25.0 | 88.7 |
| | Corn starch | — | — | 9.3 |
| | Microcrystalline cellulose (PH-102) | 74.4 | 74.4 | — |
| | Mg-stearate | 0.6 | 0.6 | — |
| | Na-stearyl fumarate | — | — | 2.0 |
| | Total | 100.0 | 100.0 | 100.0 |

The oral disintegration time, hardness, and thickness of the product tablets were measured; and the absolute hardness and HDBI thereof were calculated. The results are tabulated in Table 2-3 to show the physical properties of the product tablets. The tablets prepared in Comparative Examples 1-1 to 1-3 lack either the particular ingredients of the present invention or microcrystalline cellulose in their outer layer; and although the tablet of Comparative Example 1-1 barely managed to reach the oral disintegration time of 30 seconds or less and the absolute hardness of 2.0 N/mm$^2$ or more, the tablets of the other Comparative Examples had a low absolute-hardness. In particular, all the tablets in the Comparative Examples had a low HDBI value, i.e., less than 0.1, in which HDBI indicates the balance of the hardness and disintegrability.

TABLE 2-3

| | Physical properties of the tablets | | |
|---|---|---|---|
| | Comp. Ex. 1-1 | Comp. Ex. 1-2 | Comp. Ex. 1-3 |
| Oral disintegration time (sec) | 28 | 16 | 15 |
| Absolute hardness (N/mm$^2$) | 2.0 | 1.3 | 1.4 |
| HDBI | 0.07 | 0.08 | 0.09 |

Comparative Example 1-4

Tablet without the Particular Ingredients (i.e. Tablet with the Outer Layer of Patent Reference 2) (Case 2)

A formulation was prepared in the same manner as Example 1-1 according to the formula shown in Table 2-4 (i.e. a similar formula to that of the formulation example in Patent Reference 2), wherein its outer layer does not comprise the particular ingredients and the like of the present invention. The final compression into tablet was carried out at a pressure of 10 kN. Note that the die and punch used herein were applied with a small amount of magnesium stearate. Cellactose 80 employed herein was manufactured by MEGGLE co., Ltd.

TABLE 2-4

| | | Formula (mg) |
|---|---|---|
| | | Comp. Ex. 1-4 |
| Inner core | Microcrystalline cellulose (CELPHERE CP-203) | 50.00 |
| Outer layer | Cellactose 80 (lactose and granulation product of powder cellulose) | 180.00 |
| | Mg-stearate | Trace amount |
| | Total | 230.0 |

TABLE 2-5

| | | Formulation ratio in the outer layer (wt %) |
|---|---|---|
| | | Comp. Ex. 1-4 |
| Outer layer | Cellactose 80 (lactose and granulation product of powder cellulose) | 100.0 |
| | Mg-stearate | Trace amount |
| | Total | 100.0 |

The oral disintegration time, hardness and thickness of the product tablet were measured; and the absolute hardness and HDBI thereof were calculated. The results are tabulated in Table 2-6 to show the physical properties of the product tablet. The product tablet did not disintegrate in the oral cavity.

TABLE 2-6

| Physical properties of the tablet | |
|---|---|
| | Comparative Example 1-4 |
| Oral disintegration time (sec) | 120 or more |
| Absolute hardness (N/mm$^2$) | 3.7 |
| HDBI | 0.03 or less |

Comparative Example 1-5

Tablet without the Particular Ingredients (i.e. Tablet with the Outer Layer of Patent Reference 1) (Case 3)

A formulation was prepared in the same manner as Example 1-1 according to the formula shown in Table 2-7, wherein its outer layer does not comprise the particular ingredients of the present invention. The final compression into tablet was carried out at a pressure of 10 kN. The ingredients of the outer layer and the ratio thereof used herein were the same as those used in Test Example 6 of Patent Reference 1 (60 mg of erythritol, 19.5 mg of microcrystalline cellulose, and 0.5 mg of magnesium stearate).

TABLE 2-7

| | | Formula (mg) |
|---|---|---|
| | | Comparative Example 1-5 |
| Inner core | Microcrystalline cellulose spheres (CELPHERE CP-203) | 50.00 |
| Outer layer | Erythritol | 135.00 |
| | Microcrystalline cellulose (CEOLUS PH-102) | 43.90 |
| | Mg-stearate | 1.10 |
| | Total | 230.0 |

TABLE 2-8

| | | Formulation ratio in the outer layer (wt %) |
|---|---|---|
| | | Comparative Example 1-5 |
| Outer layer | Erythritol | 75.0 |
| | Microcrystalline cellulose (CEOLUS PH-102) | 24.4 |
| | Mg-stearate | 0.6 |
| | Total | 100.0 |

The oral disintegration time, hardness and thickness of the product tablet were measured; and the absolute hardness and HDBI thereof were calculated. The results are tabulated in Table 2-9 to show the physical properties of the product tablet. When the press-coated tablet containing unformable particles was prepared by using the outer layer described in Test Example 6 of Patent Reference 1, the oral disintegration time thereof was fast but the absolute hardness thereof was insufficient and low (i.e., less than 1 N/mm$^2$).

Thus, it was concluded that when the ingredients of the outer layer disclosed in Patent Reference 1 were used to prepare a press-coated tablet whose inner core contains particles without formability, the prepared tablet could not provide a sufficient hardness for the whole tablet.

TABLE 2-9

| | Physical properties of the tablet |
|---|---|
| | Comparative Example 1-5 |
| Oral disintegration time (sec) | 12 |
| Absolute hardness (N/mm$^2$) | 0.4 |
| HDBI | 0.03 |

Examples 2-1 to 2-6 and Comparative Example 2-1

Ratio of Microcrystalline Cellulose

Several formulations were prepared in the same manner as Example 1-1 according to the formulae shown in Table 3-1, wherein each amount of microcrystalline cellulose in the outer layer is different from each other. The final compression into tablet was carried out at a pressure of 15 kN in Comparative Example 2-1 and Examples 2-1 to 2-3, 10 kN in Example 2-4, and 4 kN in Examples 2-5 and 2-6.

TABLE 3-1

| | | Formula (mg) | | | | | | |
|---|---|---|---|---|---|---|---|---|
| | | Comp. Ex. 2-1 | Ex. 2-1 | Ex. 2-2 | Ex. 2-3 | Ex. 2-4 | Ex. 2-5 | Ex. 2-6 |
| Inner core | Microcrystalline cellulose (CELPHERE CP-203) | 50.0 | 50.0 | 50.0 | 50.0 | 50.0 | 50.0 | 50.0 |
| Outer layer | D-Mannitol | 165.6 | 149.4 | 131.4 | 113.4 | 95.4 | 41.4 | 0.9 |
| | Crospovidone | 9.0 | 9.0 | 9.0 | 9.0 | 9.0 | 9.0 | 14.4 |
| | Microcrystalline cellulose (KG-802) | — | 18.0 | 36.0 | 54.0 | 72.0 | 126.0 | 161.1 |
| | Microcrystalline cellulose (KG-1000) | 1.8 | — | — | — | — | — | — |
| | Na-stearyl fumarate | 3.6 | 3.6 | 3.6 | 3.6 | 3.6 | 3.6 | 3.6 |
| | Total | 230.0 | 230.0 | 230.0 | 230.0 | 230.0 | 230.0 | 230.0 |

TABLE 3-2

| | | Formulation ratio in the outer layer (wt %) | | | | | | |
|---|---|---|---|---|---|---|---|---|
| | | Comp. Ex. 2-1 | Ex. 2-1 | Ex. 2-2 | Ex. 2-3 | Ex. 2-4 | Ex. 2-5 | Ex. 2-6 |
| Outer layer | D-Mannitol | 92.0 | 83.0 | 73.0 | 63.0 | 53.0 | 23.0 | 0.5 |
| | Crospovidone | 5.0 | 5.0 | 5.0 | 5.0 | 5.0 | 5.0 | 8.0 |
| | Microcrystalline cellulose (KG-802) | — | 10.0 | 20.0 | 30.0 | 40.0 | 70.0 | 89.5 |
| | Microcrystalline cellulose (KG-1000) | 1.0 | — | — | — | — | — | — |
| | Na-stearyl fumarate | 2.0 | 2.0 | 2.0 | 2.0 | 2.0 | 2.0 | 2.0 |
| | Total | 100.0 | 100.0 | 100.0 | 100.0 | 100.0 | 100.0 | 100.0 |

The oral disintegration time, hardness and thickness of the product tablet were measured; and the absolute hardness and HDBI thereof were calculated. The results are tabulated in Table 3-3 to show the physical properties of the product tablet. When the content of microcrystalline cellulose in the outer layer was 1% as in Comparative Example 2-1, the tablet had an absolute hardness of lower than 2.0 N/mm$^2$ and a low value of HDBI which is an index of the balance of the hardness and disintegrability. In contrast, when the content of microcrystalline cellulose in the outer layer was 10 to 90% as in Examples 2-1 to 2-6, the tablets attained the oral disintegration time of 30 seconds or less, the absolute hardness of 2.0 N/mm$^2$ or more, and a high value of HDBI which is an index of the balance of the hardness and disintegrability.

From the viewpoint of the feeling in the oral cavity, a preferred content of the microcrystalline cellulose in the outer layer was 70% or less because tablets with a high content thereof had a sandy feeling in administration. On the other hand, from the viewpoint of hardness, a preferred content of the microcrystalline cellulose in the outer layer was 20% or more because these tablets had an absolute hardness of 2.5 N/mm$^2$ or more. Furthermore, in the cases where the content of the microcrystalline cellulose in the outer layer was 20 to 30%, the tablets attained the highest value of HDBI which is an index of the balance of the hardness and disintegrability.

TABLE 3-3

Physical properties of the tablets

|  | Comp. Ex. 2-1 | Ex. 2-1 | Ex. 2-2 | Ex. 2-3 | Ex. 2-4 | Ex. 2-5 | Ex. 2-6 |
|---|---|---|---|---|---|---|---|
| Oral disintegration time (sec) | 11 | 11 | 14 | 15 | 19 | 20 | 28 |
| Absolute hardness (N/mm$^2$) | 1.2 | 2.0 | 2.9 | 3.2 | 3.5 | 3.3 | 4.1 |
| HDBI | 0.11 | 0.19 | 0.21 | 0.21 | 0.18 | 0.17 | 0.15 |

Examples 3-1 to 3-2 and Comparative Example 3-1 to 3-2

Ratio of the Particular Ingredients (Crospovidone)

Several formulations were prepared in the same manner as Example 1-1 according to the formulae shown in Table 4-1, wherein each amount of crospovidone in the outer layer is different from each other. The final compression into tablet was carried out at a pressure of 15 kN in Comparative Example 3-1 and Example 3-1, 10 kN in Example 3-2, and 4 kN in Comparative Example 3-2.

TABLE 4-1

Formula (mg)

|  |  | Comp. Ex. 3-1 | Ex. 3-1 | Ex. 3-2 | Comp. Ex. 3-2 |
|---|---|---|---|---|---|
| Inner core | Microcrystalline cellulose (CELPHERE CP-203) | 50.0 | 50.0 | 50.0 | 50.0 |
| Outer layer | D-Mannitol | 156.6 | 131.4 | 122.4 | 68.4 |
|  | Crospovidone | 1.8 | 9.0 | 36.0 | 72.0 |
|  | Microcrystalline cellulose (KG-802) | 18.0 | 36.0 | 18.0 | 36.0 |
|  | Na-stearyl fumarate | 3.6 | 3.6 | 3.6 | 3.6 |
|  | Total | 230.0 | 230.0 | 230.0 | 230.0 |

TABLE 4-2

Formulation ratio in the outer layer (wt %)

|  |  | Comp. Ex. 3-1 | Ex. 3-1 | Ex. 3-2 | Comp. Ex. 3-2 |
|---|---|---|---|---|---|
| Outer layer | D-Mannitol | 87.0 | 73.0 | 68.0 | 38.0 |
|  | Crospovidone | 1.0 | 5.0 | 20.0 | 40.0 |
|  | Microcrystalline cellulose (KG-802) | 10.0 | 20.0 | 10.0 | 20.0 |
|  | Na-stearyl fumarate | 2.0 | 2.0 | 2.0 | 2.0 |
|  | Total | 100.0 | 100.0 | 100.0 | 100.0 |

The oral disintegration time, hardness and thickness of the product tablet were measured; and the absolute hardness and HDBI thereof were calculated. The results are tabulated in Table 4-3 to show the physical properties of the product tablets. When the content of crospovidone in the outer layer was 5 to 20% as in Examples 3-1 and 3-2, the tablets attained the oral disintegration time of 30 seconds or less, the absolute hardness of 2.0 N/mm$^2$ or more, and a high value of HDBI which is an index the balance of the hardness and disintegrability. In contrast, when the content of crospovidone in the outer layer was too low (namely 1%) or too high (namely 40%) as in Comparative Examples 3-1 and 3-2, either of the tablets had a low value of HDBI which is an index of the balance of the hardness and disintegrability.

TABLE 4-3

Physical properties of the tablets

|  | Comp. Ex. 3-1 | Ex. 3-1 | Ex. 3-2 | Comp. Ex. 3-2 |
|---|---|---|---|---|
| Oral disintegration time (sec) | 21 | 14 | 19 | 27 |
| Absolute hardness (N/mm$^2$) | 2.2 | 2.9 | 2.8 | 2.4 |
| HDBI | 0.10 | 0.21 | 0.15 | 0.09 |

Examples 4-1 to 4-2 and Comparative Example 4-1

Ratio of the Particular Ingredients (Corn Starch)

Several formulations were prepared in the same manner as Example 1-1 according to the formulae shown in Table 5-1, wherein each amount of corn starch in the outer layer is different from each other. The final compression into tablet was carried out at a pressure of 10 kN in Comparative Example 4-1 and Example 4-1, and 15 kN in Example 4-2.

TABLE 5-1

Formula (mg)

|  |  | Comp. Ex. 4-1 | Ex. 4-1 | Ex. 4-2 |
|---|---|---|---|---|
| Inner core | Microcrystalline cellulose (CELPHERE CP-203) | 50.0 | 50.0 | 50.0 |
| Outer layer | D-Mannitol | 120.6 | 131.4 | 50.4 |
|  | Corn starch | 1.8 | 9.0 | 72.0 |
|  | Microcrystalline cellulose (KG-802) | 54.0 | 36.0 | 54.0 |
|  | Na-stearyl fumarate | 3.6 | 3.6 | 3.6 |
|  | Total | 230.0 | 230.0 | 230.0 |

TABLE 5-2

Formulation ratio in the outer layer (wt %)

|  |  | Comp. Ex. 4-1 | Ex. 4-1 | Ex. 4-2 |
|---|---|---|---|---|
| Outer layer | D-Mannitol | 67.0 | 73.0 | 28.0 |
|  | Corn starch | 1.0 | 5.0 | 40.0 |
|  | Microcrystalline cellulose (KG-802) | 30.0 | 20.0 | 30.0 |
|  | Na-stearyl fumarate | 2.0 | 2.0 | 2.0 |
|  | Total | 100.0 | 100.0 | 100.0 |

The oral disintegration time, hardness, and thickness of the product tablets were measured; and the absolute hardness and HDBI thereof were calculated. The results are tabulated in Table 5-3 to show the physical properties of the product tablets. When the content of corn starch in the outer layer was 5 to 40% as in Examples 4-1 and 4-2, the tablets attained the oral disintegration time of 30 seconds or less, the absolute hardness of 2.0 N/mm$^2$ or more, and a high value of HDBI which is an index of the balance of the hardness and disintegrability. In contrast, when the content of corn starch in the outer layer was too low (namely 1%) as in Comparative Example 4-1, the tablet had a slow oral-disintegration-time of at least 30 seconds, and also a low value of HDBI which is an index of the balance of the hardness and disintegrability.

TABLE 5-3

Physical properties of the tablets

|  | Comp. Ex. 4-1 | Ex. 4-1 | Ex. 4-2 |
|---|---|---|---|
| Oral disintegration time (sec) | 38 | 15 | 20 |
| Absolute hardness (N/mm$^2$) | 3.1 | 2.1 | 3.4 |
| HDBI | 0.08 | 0.15 | 0.17 |

Examples 5-1 to 5-4

Type of Microcrystalline Cellulose

Several formulations were prepared in the same manner as Example 1-1 according to the formulae shown in Table 6-1, wherein each type of microcrystalline cellulose in the outer layer is different from each other. The final compression into tablet was carried out at a pressure of 15 kN.

TABLE 6-1

Formula (mg)

|  |  | Ex. 5-1 | Ex. 5-2 | Ex. 5-3 | Ex. 5-4 |
|---|---|---|---|---|---|
| Inner core | Microcrystalline cellulose (CELPHERE CP-203) | 50.0 | 50.0 | 50.0 | 50.0 |
| Outer layer | D-Mannitol | 131.4 | 131.4 | 131.4 | 149.4 |
|  | Crospovidone | 9.0 | 9.0 | 9.0 | 9.0 |
|  | Microcrystalline cellulose (KG-802) | 36.0 | — | — | — |
|  | Microcrystalline cellulose (PH-102) | — | 36.0 | — | — |
|  | Microcrystalline cellulose (PH-301) | — | — | 36.0 | — |
|  | Microcrystalline cellulose (KG-1000) | — | — | — | 18.0 |
|  | Na-stearyl fumarate | 3.6 | 3.6 | 3.6 | 3.6 |
|  | Total | 230.0 | 230.0 | 230.0 | 230.0 |

TABLE 6-2

Formulation ratio in the outer layer (wt %)

|  |  | Ex. 5-1 | Ex. 5-2 | Ex. 5-3 | Ex. 5-4 |
|---|---|---|---|---|---|
| Outer layer | D-Mannitol | 73.0 | 73.0 | 73.0 | 83.0 |
|  | crospovidone | 5.0 | 5.0 | 5.0 | 5.0 |
|  | Microcrystalline cellulose (KG-802) | 20.0 | — | — | — |
|  | Microcrystalline cellulose (PH-102) | — | 20.0 | — | — |
|  | Microcrystalline cellulose (PH-301) | — | — | 20.0 | — |
|  | Microcrystalline cellulose (KG-1000) | — | — | — | 10.0 |
|  | Na-stearyl fumarate | 2.0 | 2.0 | 2.0 | 2.0 |
|  | Total | 100.0 | 100.0 | 100.0 | 100.0 |

The oral disintegration time, hardness, and thickness of the product tablets were measured; and the absolute hardness and HDBI thereof were calculated. The results are tabulated in Table 6-3 to show the physical properties of the product tablet. Although each type of microcrystalline cellulose in the outer layer varied as in Examples 5-1 to 5-4, all the tablets attained the oral disintegration time of 30 seconds or less, the absolute hardness of 2.0 N/mm$^2$ or more, and a high value of HDBI which is an index of the balance of the hardness and disintegrability. When KG-802 or KG-1000 was used as microcrystalline cellulose of the outer layer, either of the tablets attained the HDBI value of 0.2 or more (wherein HDBI is an index of the balance of the hardness and disintegrability) to give a tablet with a preferred balance.

TABLE 6-3

Physical properties of the tablets

|  | Ex. 5-1 | Ex. 5-2 | Ex. 5-3 | Ex. 5-4 |
|---|---|---|---|---|
| Oral disintegration time (sec) | 14 | 11 | 12 | 12 |
| Absolute hardness (N/mm$^2$) | 2.9 | 2.1 | 2.0 | 2.3 |
| HDBI | 0.21 | 0.19 | 0.17 | 0.20 |

Examples 6-1 to 6-3

Types of Lubricant

Several formulations were prepared in the same manner as Example 1-1 according to the formulae shown in Table 7-1, wherein each type of lubricant in the outer layer is different from each other. The final compression into tablet was carried out at a pressure of 15 kN.

TABLE 7-1

Formula (mg)

|  |  | Ex. 6-1 | Ex. 6-2 | Ex. 6-3 |
|---|---|---|---|---|
| Inner core | Microcrystalline cellulose (CELPHERE CP-203) | 50.0 | 50.0 | 50.0 |
| Outer layer | D-Mannitol | 131.4 | 133.2 | 133.2 |
|  | Crospovidone | 9.0 | 9.0 | 9.0 |
|  | Microcrystalline cellulose (KG-802) | 36.0 | 36.0 | 36.0 |
|  | Na-stearyl fumarate | 3.6 | — | — |
|  | Sucrose fatty acid ester | — | 1.8 | — |
|  | Mg-stearate | — | — | 1.8 |
|  | Total | 230.0 | 230.0 | 230.0 |

TABLE 7-2

Formulation ratio in the outer layer (wt %)

|  |  | Ex. 6-1 | Ex. 6-2 | Ex. 6-3 |
|---|---|---|---|---|
| Outer layer | D-Mannitol | 73.0 | 74.0 | 74.0 |
|  | Crospovidone | 5.0 | 5.0 | 5.0 |
|  | Microcrystalline cellulose (KG-802) | 20.0 | 20.0 | 20.0 |
|  | Na-stearyl fumarate | 2.0 | — | — |
|  | Sucrose fatty acid ester | — | 1.0 | — |
|  | Mg-stearate | — | — | 1.0 |
|  | Total | 100.0 | 100.0 | 100.0 |

The oral disintegration time, hardness, and thickness of the product tablets were measured; and the absolute hardness and HDBI thereof were calculated. The results are tabulated in Table 7-3 to show the physical properties of the product tablet. Although each type of lubricant in the outer layer varied as in Examples 6-1 to 6-3, all the tablets attained the oral disintegration time of 30 seconds or less, the absolute hardness of 2.0 N/mm² or more, and a high value of HDBI which is an index of the balance of the hardness and disintegrability.

TABLE 7-3

Physical properties of the tablets

|  | Ex. 6-1 | Ex. 6-2 | Ex. 6-3 |
|---|---|---|---|
| Oral disintegration time (sec) | 14 | 13 | 15 |
| Absolute hardness (N/mm²) | 2.9 | 4.0 | 2.8 |
| HDBI | 0.21 | 0.30 | 0.19 |

Examples 7-1 to 7-5

Combining Several Particular Ingredients

Several formulations were prepared in the same manner as Example 1-1 according to the formulae shown in Table 8-1, wherein two or more particular ingredients are contained in the outer layer. The final compression into tablet was carried out at a pressure of 10 kN in Examples 7-1 and 7-3, and 15 kN in the other Examples.

TABLE 8-1

Formula (mg)

|  |  | Ex. 7-1 | Ex. 7-2 | Ex. 7-3 | Ex. 7-4 | Ex. 7-5 |
|---|---|---|---|---|---|---|
| Inner core | Microcrystalline cellulose (CELPHERE CP-203) | 50.0 | 50.0 | 50.0 | 50.0 | 50.0 |
| Outer layer | D-Mannitol | 113.4 | 113.4 | 66.6 | 134.5 | 118.3 |
|  | Corn starch | 18.0 | 18.0 | 36.0 | 14.9 | 13.1 |
|  | Crospovidone | — | — | — | 9.0 | 9.0 |
|  | Carmellose | 3.6 | 3.6 | 7.2 | — | — |
|  | L-HPC (LH-21) | 7.2 | 7.2 | 14.4 | — | — |
|  | Microcrystalline cellulose (KG-802) | — | 36.0 | — | 18.0 | 36.0 |
|  | Microcrystalline cellulose (KG-1000) | 36.0 | — | 54.0 | — | — |
|  | Na-stearyl fumarate | — | — | — | 3.6 | 3.6 |
|  | Mg-stearate | 1.8 | 1.8 | 1.8 | — | — |
|  | Total | 230.0 | 230.0 | 230.0 | 230.0 | 230.0 |

TABLE 8-2

Formulation ratio in the outer layer (wt %)

|  |  | Ex. 7-1 | Ex. 7-2 | Ex. 7-3 | Ex. 7-4 | Ex. 7-5 |
|---|---|---|---|---|---|---|
| Outer layer | D-Mannitol | 63.0 | 63.0 | 37.0 | 74.7 | 65.7 |
|  | Corn starch | 10.0 | 10.0 | 20.0 | 8.3 | 7.3 |
|  | Crospovidone | — | — | — | 5.0 | 5.0 |
|  | Carmellose | 2.0 | 2.0 | 4.0 | — | — |
|  | L-HPC (LH-21) | 4.0 | 4.0 | 8.0 | — | — |
|  | Microcrystalline cellulose (KG-802) | — | 20.0 | — | 10.0 | 20.0 |
|  | Microcrystalline cellulose (KG-1000) | 20.0 | — | 30.0 | — | — |
|  | Na-stearyl fumarate | — | — | — | 2.0 | 2.0 |
|  | Mg-stearate | 1.0 | 1.0 | 1.0 | — | — |
|  | Total | 100.0 | 100.0 | 100.0 | 100.0 | 100.0 |

The oral disintegration time, hardness, and thickness of the product tablets were measured; and the absolute hardness and HDBI thereof were calculated. The results are tabulated in Table 8-3 to show the physical properties of the product tablet. Even in the cases where the outer layer comprised two or more particular ingredients, the tablets attained the oral disintegration time of 30 seconds or less, the absolute hardness of 2.0 N/mm² or more, and a high value of HDBI which is an index of the balance of the hardness and disintegrability. The porosity of the outer layer was 9% in Example 7-1, and 10% in Example 7-3.

TABLE 8-3

Physical properties of the tablet

|  | Ex. 7-1 | Ex. 7-2 | Ex. 7-3 | Ex. 7-4 | Ex. 7-5 |
|---|---|---|---|---|---|
| Oral disintegration time (sec) | 15 | 18 | 20 | 11 | 13 |
| Absolute hardness (N/mm²) | 2.2 | 2.7 | 3.2 | 2.2 | 2.8 |
| HDBI | 0.15 | 0.15 | 0.16 | 0.19 | 0.21 |

Examples 8-1 to 8-2

Thickness Ratio of the Inner Core

Two formulations were prepared according to the formulae shown in Table 9-1, wherein each thickness ratio of the inner core is different from each other. Firstly, the ingredients of the outer layer were mixed. The mixture of the outer layer in an amount indicated in each column of "Weight of outer layer (under-portion)" in Table 9-1 was placed in a die with a diameter indicated in each column of "Inner core" in Table 9-1. The die was gently shaken to smooth the surface of the powder. On the mixture, the amount of microcrystalline cellulose spheres (CELPHERE CP-203) indicated in the table was put, and the layered material was temporarily pressed at a low pressure of 3 kN using a hand press machine (oil hydraulic press system, manufactured by RIKEN). This temporarily-pressed substance was placed on a punch (8 mm diameter) concentrically in a manner to make the under-portion of the outer layer placed downward. A die (8 mm, diameter) was covered thereon, and the additional above-mentioned mixture of the ingredients of the outer layer in an amount indicated in each column of "Weight of outer layer (side- and upper-portions)" in Table 9-1 was added therein. The composition between the punch and the die was finally pressed to prepare the press-coated orally-disintegrating tablets. The final compression into tablet was carried out at a pressure of 4 kN.

TABLE 9-1

Formula (mg)

|  |  | Ex. 8-1 | Ex. 8-2 |
|---|---|---|---|
| Structure | Inner core | Diameter 6 mm | Diameter 6 mm |
|  | Weight of outer layer (under-portion) | 40 mg | 30 mg |
|  | Weight of outer layer (side- and upper-portions) | 140 mg | 110 mg |
| Inner core | Microcrystalline cellulose (CELPHERE CP-203) | 50.00 | 50.00 |
| Outer layer | D-Mannitol | 41.40 | 41.40 |
|  | Crospovidone | 9.00 | 9.00 |
|  | Microcrystalline cellulose (KG-802) | 126.00 | 126.00 |
|  | Na-stearyl fumarate | 3.60 | 3.60 |
|  | Total | 230.0 | 230.0 |

TABLE 9-2

| | Formulation ratio in the outer layer (wt %) | | |
|---|---|---|---|
| | | Ex. 8-1 | Ex. 8-2 |
| Outer layer | D-Mannitol | 23.0 | 23.0 |
| | Crospovidone | 5.0 | 5.0 |
| | Microcrystalline cellulose (KG-802) | 70.0 | 70.0 |
| | Na-stearyl fumarate | 2.0 | 2.0 |
| | Total | 100.0 | 100.0 |

The oral disintegration time, hardness, and thickness of the product tablets were measured; and the absolute hardness and HDBI thereof were calculated. The results are tabulated in Table 9-3 to show the physical properties of the product tablet. In the cases where the thickness ratio of inner core was 32 to 54%, the tablets attained the oral disintegration time of 30 seconds or less, the absolute hardness of 2.0 N/mm$^2$ or more, and a high value of HDBI which is an index of the balance of the hardness and disintegrability.

TABLE 9-3

| Physical properties of the tablet | | |
|---|---|---|
| | Example 8-1 | Example 8-2 |
| Oral disintegration time (sec) | 20 | 14 |
| Absolute hardness (N/mm$^2$) | 3.3 | 2.2 |
| HDBI | 0.17 | 0.16 |
| Thickness of tablet (mm) | 3.82 | 3.79 |
| Thickness of inner core (mm) | 1.23 | 2.03 |
| Thickness ratio of inner core (%) | 32 | 54 |

Example 9-1

Press-Coated Orally-Disintegrating Tablets Comprising an Active Ingredient (1) Preparation of Acetaminophen-Containing Particles (Manufactured by Asahi Easel Chemicals Co., Ltd.)

Acetaminophen was coated to prepare acetaminophen-containing particles whose coating-rate is 10 wt %. The coating material used herein comprises AQUACOAT™ (manufactured by Asahi Kasei Chemical Co., Ltd), triacetin and mannitol in a ratio of 100:25:50 (wt %), respectively. A formulation containing the active ingredient was prepared in the same manner as Example 1-1 according to the formula shown in Table 10-1. The final compression into tablet was carried out at a pressure of 4 kN.

TABLE 10-1

| | Formula (mg) | |
|---|---|---|
| | | Example 9-1 |
| Inner core | Acetaminophen-containing particles | 28.57 |
| | Crospovidone (Polyplasdone XL-10) | 10.71 |
| | Talc | 10.71 |
| Outer layer | D-Mannitol | 131.40 |
| | Crospovidone | 9.00 |
| | Microcrystalline cellulose (KG-802) | 36.00 |
| | Na-stearyl fumarate | 3.60 |
| | Total | 230.0 |

TABLE 10-2

| | Formulation ratio in the outer layer (wt %) | |
|---|---|---|
| | | Example 9-1 |
| Outer layer | D-Mannitol | 73.0 |
| | Crospovidone | 5.0 |
| | Microcrystalline cellulose (KG-802) | 20.0 |
| | Na-stearyl fumarate | 2.0 |
| | Total | 100.0 |

The oral disintegration time, hardness, and thickness of the product tablet were measured; and the absolute hardness and HDBI thereof were calculated. The results are tabulated in Table 10-3 to show the physical properties of the product tablet. The tablet attained the oral disintegration time of 30 seconds or less, the absolute hardness of 2.0 N/mm$^2$ or more, and a high value of HDBI which is an index of the balance of the hardness and disintegrability. Thus, it was concluded that the tablet comprising the active ingredient can also provide a press-coated orally-disintegrating tablet with good properties.

TABLE 10-3

| Physical properties of the tablet | |
|---|---|
| | Example 9-1 |
| Oral disintegration time (sec) | 18 |
| Absolute hardness (N/mm$^2$) | 3.2 |
| HDBI | 0.17 |

(2) Preparation of Particle Comprising Gasmotin

To 567 g of purified water was added 31.5 g of polysorbate 80 [Japanese Pharmacopoeia polysorbate 80 (HX): manufactured by NOF Co., Ltd.] and the mixture was well mixed. Then, 73.5 g of talc (manufactured by Hayashi Kasei Co., Ltd.) and 52.5 g of croscarmellose sodium (Ac-Di-Sol: manufactured by FMC BioPolymer Co., Ltd.) were added thereto and the mixture was well stirred ("Mixture I"). Separately, another solution of sodium hydroxide (2.85 g) in purified water (67.65 g) was slowly added to 705 g of methacrylic copolymer LD (POLYQUID PA-30S: manufactured by Sanyo Chemical Industries Ltd.) and the mixture was stirred ("Mixture II"). To Mixture I was added Mixture II to be suspended. The suspension was sieved through a mesh (177 µm) to obtain a coating dispersion.

346.5 g of Gasmotin and 3.5 g of light anhydrous silicic acid (Aerosil 200: manufactured by Nippon Aerosil Co., Ltd.) were sieved through a mesh (500 µm) and mixed well in a polyethylene bag to prepare a drug-containing composition. Then, the composition was put into a Wurster-fluid bed granulator equipped with forced circulation device (improved Wurster-fluidized bet granulator, MP-01 SPC, manufactured by Powrex Co.), and sprayed with the coating dispersion prepared above. The spraying was performed at an inlet air temperature of 80° C. to 90° C. and the outlet air temperature of 26° C. to 30° C., and the production was performed while spraying the spray liquid from a bottom spray at a flow of 10 g/min to 12 g/min, spray air flow of 80 L/min, spray air pressure of 0.2 MPa to 0.3 MPa, side air pressure of 0.20 MPa to 0.25 MPa, and inlet air flow of about 0.30 m$^3$/min to 0.55 m$^3$/min. The coating was completed when the amount of coating dispersion was about 1306 g, and the resulting particles were dried until the outlet air temperature reached 42° C. The obtained particles were sieved through a 32 mesh (opening: 500 µm) sieve to prepare drug-containing particles having a mean particle size of about 165 µm.

A formulation containing the particles comprising the active ingredient in the inner core was prepared according to the formula shown in Table 11-1. Mixture of the Gasmotin-containing particles, crospovidone and talc were used in the inner core. Firstly, the ingredients of the outer layer were mixed. A portion of the mixture (40 mg) was placed in a die (6 mm diameter) and the die was gently shaken to smooth the surface of the powder (which is the under-portion of the outer layer). On the mixture, 50 mg of the mixture of the inner core were put, and then the layered material was temporarily pressed at a low pressure (3 kN) using a hand press machine (oil hydraulic press system, manufactured by RIKEN). This temporarily-pressed substance was placed on a punch (8 mm diameter) concentrically in a manner to make the under-portion of the outer layer placed downward. A die (8 mm diameter) was covered thereon, and the additional above-mentioned mixture of the ingredients of the outer layer (for the side- and upper-portions of the outer layer, 140 mg) was put on the temporarily-pressed substance. The composition between the punch and the die was finally pressed at a pressure of 4 kN to prepare the desired press-coated orally-disintegrating tablets.

TABLE 11-1

| | Formula (mg) | |
|---|---|---|
| | | Example 9-2 |
| Inner core | Gasmotin containing particle | 28.57 |
| | Crospovidone (Polyplasdone XL-10) | 10.71 |
| | Talc | 10.71 |
| Outer layer | D-Mannitol | 41.40 |
| | Crospovidone | 9.00 |
| | Microcrystalline cellulose (KG-802) | 126.00 |
| | Na-stearyl fumarate | 3.60 |
| | Total | 230.0 |

TABLE 11-2

| | Formulation ratio in the outer layer (wt %) | |
|---|---|---|
| | | Example 9-2 |
| Outer layer | D-Mannitol | 23.0 |
| | Crospovidone | 5.0 |
| | Microcrystalline cellulose (KG-802) | 70.0 |
| | Na-stearyl fumarate | 2.0 |
| | Total | 100.0 |

The oral disintegration time, hardness and thickness of the product tablet were measured; and the absolute hardness and HDBI thereof were calculated. The results are tabulated in Table 11-3 to show the physical properties of the product tablet. The tablet attained the oral disintegration time of 30 seconds or less, the absolute hardness of 2.0 N/mm² or more, and a high value of HDBI which is an index of the balance of the hardness and disintegrability. Thus, it was concluded that the tablet comprising the active ingredient can also provide a press-coated orally-disintegrating tablet with good properties.

TABLE 11-3

| Physical properties of the tablet | |
|---|---|
| | Example 9-2 |
| Oral disintegration time (sec) | 27 |
| Absolute hardness (N/mm²) | 4.0 |
| HDBI | 0.15 |

Comparative Examples 5-1 to 5-4

Normal Tablet (i.e. Tablet without Core)

The ingredients of the outer layer shown in Example 1-1 were used to prepare a normal tablet (i.e. a tablet which does not comprise an inner core). Firstly, the ingredients shown in Table 12-1 were homogeneously mixed in the ratio indicated in the table. The mixture (230 mg) was compressed into a tablet (8 mm diameter) at a pressure of 4, 10, 15 or 20 kN to prepare each of the normal-tablets.

TABLE 12-1

| Formula (mg) | |
|---|---|
| | Comp. Ex. 5-1 to 5-4 |
| D-Mannitol | 167.9 |
| Corn starch | 11.5 |
| Microcrystalline cellulose (KG-802) | 46.0 |
| Na-stearyl fumarate | 4.6 |
| Total | 230.0 |

TABLE 12-2

| Formulation ratio (wt %) | |
|---|---|
| | Comp. Ex. 5-1 to 5-4 |
| D-Mannitol | 73.0 |
| Corn starch | 5.0 |
| Microcrystalline cellulose (KG-802) | 20.0 |
| Na-stearyl fumarate | 2.0 |
| Total | 100.0 |

The oral disintegration time, hardness, and thickness of the product tablets were measured; and the absolute hardness and HDBI thereof were calculated. The results are tabulated in Table 12-3 to show the physical properties of the product tablet.

When the tablets were compressed at a pressure of 15 RN or more, their oral disintegration time were 30 seconds or more. When the tablet was compressed at a pressure of 4 kN, its absolute hardness was less than 1.0. Regardless of the compressing pressure, all the tablets had the HDBI value of 0.15 or less, in which HDBI is an index of the balance of the hardness and disintegrability.

TABLE 12-3

| Physical properties of the tablet | | | | |
|---|---|---|---|---|
| | Comp. Ex. 5-1 4 kN | Comp. Ex. 5-2 10 kN | Comp. Ex. 5-3 15 kN | Comp. Ex. 5-4 20 kN |
| Oral disintegration time (sec) | 17 | 26 | 39 | 45 |
| Absolute hardness (N/mm²) | 0.8 | 2.8 | 3.8 | 4.2 |
| HDBI | 0.05 | 0.11 | 0.10 | 0.09 |

Comparative Example 6-1

Normal Tablet (i.e. Tablet without Core) which Homogeneously Comprises Particles without Formability A mixture of the ingredients of the inner core and outer layer shown in Example 1-1 was used to prepare a normal tablet whose particles without formability are homogeneously distributed in the tablet. Firstly, the ingredients shown in Table 13-1 were homogeneously mixed in the ratio indicated in the table. The mixture was compressed into a tablet (8 mm diameter) at a pressure of 10 kN to prepare the normal tablet.

Note that the normal tablet was prepared in the same conditions as the press-coated tablet in Example 1-1 (e.g. each ingredient content per tablet, the weight of the tablet, the diameter of the tablet and the compressive force were the same), and the two tablets (i.e. normal tablet and press-coated tablet) were different only in the structure and the distribution of the unformable particles.

TABLE 13-1

| Formula (mg) | |
| --- | --- |
| | Comp. Ex. 6-1 |
| Microcrystalline cellulose spheres (CELPHERE CP-203) | 50.0 |
| D-Mannitol | 131.4 |
| Corn starch | 9.0 |
| Microcrystalline cellulose (KG-802) | 36.0 |
| Na-stearyl fumarate | 3.6 |
| Total (mg) | 230.0 |

TABLE 13-2

| Formulation ratio (wt %) | |
| --- | --- |
| | Comp. Ex. 6-1 |
| Microcrystalline cellulose spheres (CELPHERE CP-203) | 21.7 |
| D-Mannitol | 57.1 |
| Corn starch | 3.9 |
| Microcrystalline cellulose (KG-802) | 15.7 |
| Na-stearyl fumarate | 1.6 |
| Total | 100.0 |

The oral disintegration time, hardness, and thickness of the product tablets were measured; and the absolute hardness and HDBI thereof were calculated. As shown in Table 13-3, the normal tablet had a low absolute hardness and a slow oral-disintegration-time compared with the press-coated tablet.

Thus, regarding orally disintegrating tablets comprising a large amount of unformable particles, it was concluded that a press-coated tablet whose particles are contained internally has preferred physical-properties compared with a normal tablet whose particles are homogeneously distributed.

TABLE 13-3

| Physical properties of the tablet | | |
| --- | --- | --- |
| | Comp. Ex. 6-1 (normal tablet) | Ex. 1-1 (press-coated tablet) |
| Oral disintegration time (sec) | 26 | 14 |
| Absolute hardness (N/mm$^2$) | 1.9 | 2.1 |
| HDBI | 0.07 | 0.15 |

INDUSTRIAL APPLICABILITY

The present invention can provide a press-coated orally-disintegrating tablet wherein its inner core has poor formability and which has a preferred balance between hardness and disintegrability.

The invention claimed is:

1. A press-coated rapidly orally-disintegrating tablet with an outer layer surrounding an inner core having a powder/granular material with poor formability wherein:
   the inner core has a thickness of 30 to 80% based on that of the whole tablet; and
   the outer layer comprises (a) microcrystalline cellulose, (b) a sugar or a sugar alcohol, (c) one or more particular ingredients selected from the group consisting of crospovidone, a starch, low-substituted hydroxypropylcellulose and carmellose, and (d) one or more additional formulation ingredients,
   wherein the microcrystalline cellulose (a) is contained in an amount of 20 to 70 wt %,
   the sugar or sugar alcohol (b) is contained in an amount of 20 to 75 wt %,
   when the particular ingredients (c) comprise a starch, then the starch is contained in an amount of 3 to 40 wt %, and
   when the particular ingredients (c) comprise at least one ingredient selected from the group consisting of crospovidone, low-substituted hydroxypropylcellulose and carmellose, then the total amount of at least one of crospovidone, low-substituted hydroxypropylcellulose and carmellose is 3 to 20 wt %, provided that when the particular ingredients (c) comprise both a starch and at least one ingredient selected from the group consisting of crospovidone, low-substituted hydroxypropylcellulose and carmellose, then the total amount of the particular ingredients (c) is 6 to 43 wt %, and
   the additional formulation ingredient(s) (d) is contained in an amount of 0.01 to 25 wt %, per 100 wt % of the outer layer,
   the outer layer has a porosity of 1 to 15%, and
   the tablet has a hardness and disintegrating balance index ("HDBI") value of 0.15 N/mm$^2$ sec or more.

2. The press-coated rapidly orally-disintegrating tablet of claim 1, wherein the inner core has a porosity of 10 to 90%.

3. The press-coated rapidly orally-disintegrating tablet of claim 1, wherein
   the particular ingredient (c) is a starch; and
   the starch is contained in an amount of 3 to 40 wt % per 100 wt % of the outer layer.

4. The press-coated rapidly orally-disintegrating tablet of claim 1, wherein
   the microcrystalline cellulose (a) is contained in an amount of 20 to 70 wt % per 100 wt % of the outer layer;
   the particular ingredient (c) is a starch; and
   the starch is contained in an amount of 3 to 40 wt % per 100 wt % of the outer layer.

5. The press-coated rapidly orally-disintegrating tablet of claim 1, wherein the particular ingredient (c) is corn starch.

6. The press-coated rapidly orally-disintegrating tablet of claim 1, wherein
   the particular ingredient (c) is at least one ingredient selected from the group consisting of crospovidone, low-substituted hydroxypropylcellulose and carmellose; and
   the particular ingredient(s) (c) in total is contained in an amount of 3 to 20 wt % per 100 wt % of the outer layer.

7. The press-coated rapidly orally-disintegrating tablet of claim 1, wherein the sugar or sugar alcohol (b) is mannitol.

8. The press-coated rapidly orally-disintegrating tablet of claim 1, wherein the inner core has a thickness of 30 to 70% based on that of the whole tablet.

9. The press-coated rapidly orally-disintegrating tablet of claim 1, wherein a porosity of the inner core is greater than the porosity of the outer layer.

10. The press-coated rapidly orally-disintegrating tablet of claim 1, wherein the inner core comprises an active ingredient.

11. The press-coated rapidly orally-disintegrating tablet of claim 1, wherein the outer layer further comprises an active ingredient.

12. The press-coated rapidly orally-disintegrating tablet of claim 1, wherein the particular ingredient (c) is at least one ingredient selected from the group consisting of crospovidone, corn starch, potato starch, rice starch, wheat starch, sweet potato starch, mung bean starch, tapioca starch and partly pregelatinized starch.

13. The press-coated rapidly orally-disintegrating tablet of claim 1, wherein the additional formulation ingredient (d) is at least one ingredient selected from the group consisting of a filler, a disintegrant, a binder, a sweetening agent, a taste corrective/odor corrective, a stabilizer, a surfactant, a fluidizing agent, an antistatic agent, a coating agent, a lubricant, a colorant, and a flavor.

14. The press-coated rapidly orally-disintegrating tablet of claim 1, wherein the tablet has an absolute hardness of 2.0 $N/mm^2$ or more.

* * * * *